US011147942B2

United States Patent
Mawson (10) Patent No.: US 11,147,942 B2
(45) Date of Patent: Oct. 19, 2021

(54) ATTENUATED LOW-FREQUENCY STIMULATION (ALFS) OF SPINAL ENERGY POINTS

(71) Applicant: Kunasan LLC, Fort Collins, CO (US)

(72) Inventor: Paul Mawson, Fort Collins, CO (US)

(73) Assignee: KUNASAN LLC, Aurora, CO (US)

( * ) Notice: Subject to any disclaimer, the term of this patent is extended or adjusted under 35 U.S.C. 154(b) by 315 days.

(21) Appl. No.: 16/283,450

(22) Filed: Feb. 22, 2019

(65) Prior Publication Data

US 2019/0298966 A1    Oct. 3, 2019

Related U.S. Application Data

(60) Provisional application No. 62/648,792, filed on Mar. 27, 2018.

(51) Int. Cl.
*A61M 21/02*    (2006.01)
*A61H 39/00*    (2006.01)
(Continued)

(52) U.S. Cl.
CPC ............. *A61M 21/02* (2013.01); *A61H 39/00* (2013.01); *A61H 2039/005* (2013.01);
(Continued)

(58) Field of Classification Search
CPC ...... A61N 1/40; A63B 21/4037; G10K 11/24; A61M 21/02; A61M 2021/0011;
(Continued)

(56) References Cited

U.S. PATENT DOCUMENTS

| | | | |
|---|---|---|---|
| 5,220,332 A | | 6/1993 | Beckner et al. |
| 5,449,376 A | * | 9/1995 | Callahan ................. A61N 1/40 |
| | | | 607/2 |

(Continued)

FOREIGN PATENT DOCUMENTS

| | | | |
|---|---|---|---|
| DE | 29918884 U1 | * 1/2000 | ........... A61H 33/025 |
| WO | WO-8809685 A1 | * 12/1988 | ............... A61N 1/40 |
| WO | 2017120023 A1 | 7/2017 | |

OTHER PUBLICATIONS

Int'l Search Report and Written Opinion dated Apr. 30, 2019 for Int'l Patent Application No. PCT/US19/19253 of Kunasan LLC, filed Feb. 22, 2019, 10 pages.

*Primary Examiner* — Kaylee R Wilson
(74) *Attorney, Agent, or Firm* — Perkins Coie LLP (57) ABSTRACT

A system comprises a flexible pad, an antenna wire disposed within the flexible pad, and an electronics unit connected to or capable of being connected to the antenna wire. The electronics unit can include circuitry configured to access a stored playlist representing a sequence of tones at different frequencies, and to generate signals representing the tones such that two or more of the tones are generated in the sequence according to the stored playlist. The electronics unit further can include an oscillator to generate a carrier signal and coupled so that the signals representing the tones modulate the carrier signal according to the sequence when applied to an input of the oscillator, where the oscillator has an output connected to transmit the modulated carrier signal onto an antenna when the electronics unit is in operation.

23 Claims, 7 Drawing Sheets

(51) Int. Cl.
*H01Q 1/14* (2006.01)
*A61M 21/00* (2006.01)

(52) U.S. Cl.
CPC ............... *A61M 2021/0011* (2013.01); *A61M 2021/0055* (2013.01); *A61M 2205/52* (2013.01); *H01Q 1/14* (2013.01)

(58) Field of Classification Search
CPC ...... A61M 2021/0055; A61M 2205/52; A61M 2205/505; A61M 2021/0027; A61H 39/00; A61H 2039/005; H01Q 1/14
USPC ..................................................... 600/26–28
See application file for complete search history.

(56) References Cited

U.S. PATENT DOCUMENTS

| | | | |
|---|---|---|---|
| 9,886,965 B1 | 2/2018 | Ahmet et al. | |
| 2002/0039396 A1* | 4/2002 | Zalio .................... | G06F 1/0328 375/355 |
| 2007/0294297 A1 | 12/2007 | Kesteloot et al. | |
| 2009/0326424 A1* | 12/2009 | Shrestha ............ | A61H 23/0236 601/47 |
| 2016/0287928 A1* | 10/2016 | Darnell ............. | A63B 21/4037 |
| 2018/0071140 A1* | 3/2018 | Sheydin ............... | A61N 5/0625 |
| 2018/0256913 A1* | 9/2018 | Casanova .............. | A61N 2/006 |
| 2019/0209805 A1* | 7/2019 | Ra Speret ................ | G10H 1/00 |

\* cited by examiner

| | 174Hz | 285Hz | 396Hz | 417Hz | 528Hz | 639Hz | 741Hz | 852Hz | 963Hz |
|---|---|---|---|---|---|---|---|---|---|
| Elevation 1 | x | x | x | x | x |   | x | x | x |
| Elevation 2 | x | x | x |   | x |   | x | x |   |
| Stabilizing |   |   | x |   |   | x |   | x |   |
| Tuning | x | x | x | x | x | x | x | x | x |

# ATTENUATED LOW-FREQUENCY STIMULATION (ALFS) OF SPINAL ENERGY POINTS

This application claims the benefit of U.S. provisional patent application No. 62/648,792, filed on Mar. 27, 2018, and titled, "Portable Apparatus for Promoting Biophoton Coherence in Humans and Animals," which is incorporated by reference herein in its entirety.

FIELD OF THE INVENTION

This disclosure relates to a method and apparatus for promoting biophoton coherence in a living body by affecting the body's subtle energies known as the "biofield," and more particularly, to an apparatus and method for attenuated low-frequency stimulation (ALFS) of a body's chakra points.

BACKGROUND

The "biofield" is an electromagnetic field created by a living body, which surrounds and penetrates the body. A biofield is comprised of "biophotons," which are photons radiated from the cells of living things. Hence, biophotons are ultraweak electromagnetic radiation (i.e., light, although not necessarily of human-visible wavelengths) emanating from all living systems, including humans.

Biophoton emission is linked to the endogenous production of excited states within a living system. Plants, animals and humans generate up to 100 photons per second, per 0.15 square inches (one square centimeter) of surface area. The light is too faint to be seen by the naked eye, but biophotons have been detected and verified using photomultiplier tubes. In recent years the notion of measuring bioelectric energies as an accurate diagnostic tool has gained greater acceptance.

BRIEF DESCRIPTION OF THE DRAWINGS

One or more embodiments of the present disclosure are illustrated by way of example and not limitation in the figures of the accompanying drawings, in which like references indicate similar elements.

DETAILED DESCRIPTION

In this description, references to "an embodiment", "one embodiment" or the like, mean that the particular feature, function, structure or characteristic being described is included in at least one embodiment of the technique introduced here. Occurrences of such phrases in this specification do not necessarily all refer to the same embodiment. On the other hand, the embodiments referred to also are not necessarily mutually exclusive.

The detection and characterization of human biophoton emission has led to suggestions that it has potential applications in medicine. It is believed that a biofield can be influenced by external technologies and techniques, to beneficially influence the body from which it emanates. Introduced here, therefore, is a technology to elevate, tune and/or stabilize the biofield response of a living organism, such as (but not limited to) a human.

Figure 1:
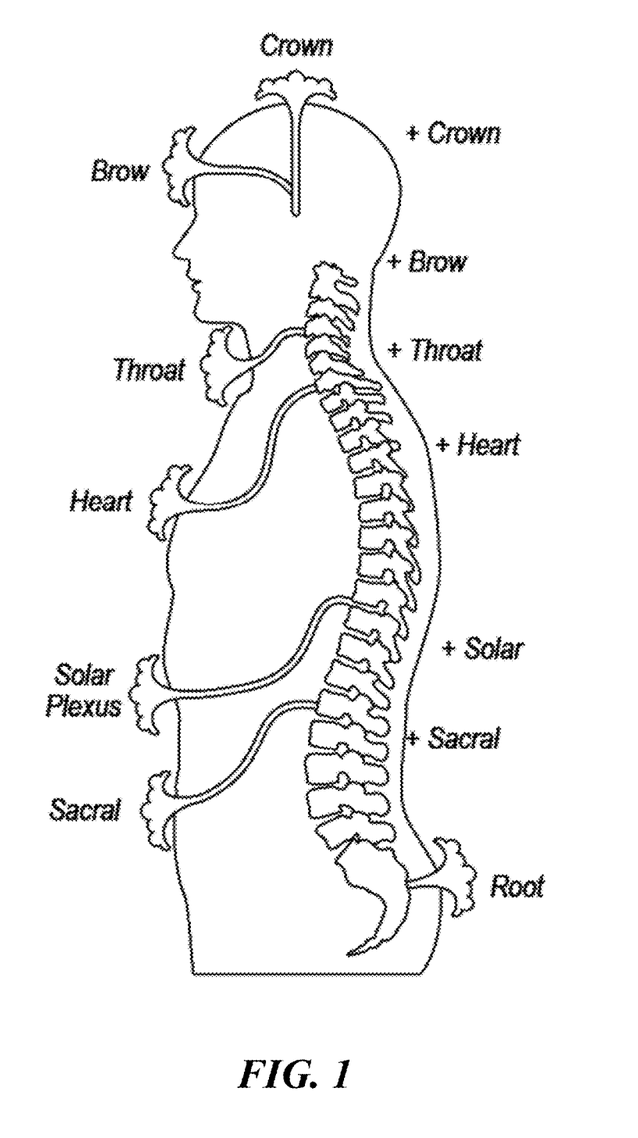
FIG. 1 illustrates the chakra points of a human.

More specifically, the technology introduced here relates to a non-invasive, non-touching method for elevating, tuning and/or stabilizing a living body's biofield by use of a technique that transmits frequencies designed to stimulate human chakra points. A chakra point, or simply "chakra," is a meeting point for an energy channel within a living body. Chakras have also been described as vortices that penetrate the body and its aura, through which various energies are received, transformed, and distributed. As shown in FIG. 1, the human body has seven main chakras, which lie in a linear pathway along the spine, from the root chakra located at the base of the spine to the crown chakra located at the top of the cranium. The seven main human chakra points are:

1) root chakra—located at the base of the spine in the coccyx (tailbone) area.

2) sacral chakra—located at in the lower abdomen, below the navel.

3) solar plexus chakra—located in the upper abdomen in the stomach area.

4) heart chakra—located in the center of the chest, just above heart.

5) throat chakra—located in the throat.

6) brow chakra—located on the forehead between the eyes.

7) crown chakra—located at the very top of the head.

It is proposed herein that elevating, tuning and/or stabilizing the biofield of a body creates or promotes the creation of coherent biophoton fields within the body. It is thought that biophoton coherence is important to a person's or animal's well-being. It has been demonstrated that electrostimulation to acupuncture hand-point JG4 showed less biophoton emission than electrostimulation to adjacent areas to JG4 point, suggesting that coherent biophotons were absorbed into the active acupuncture point. See J. Slawinski and Z. Gorski, "Imaging of Biophoton Emission from Electrostimulated Skin Acupuncture Point JG4: Effect of light enhancers." Indian Journal of Experimental Biology, vol. 46, pp. 345-352 (May 2008).

Figure 2:
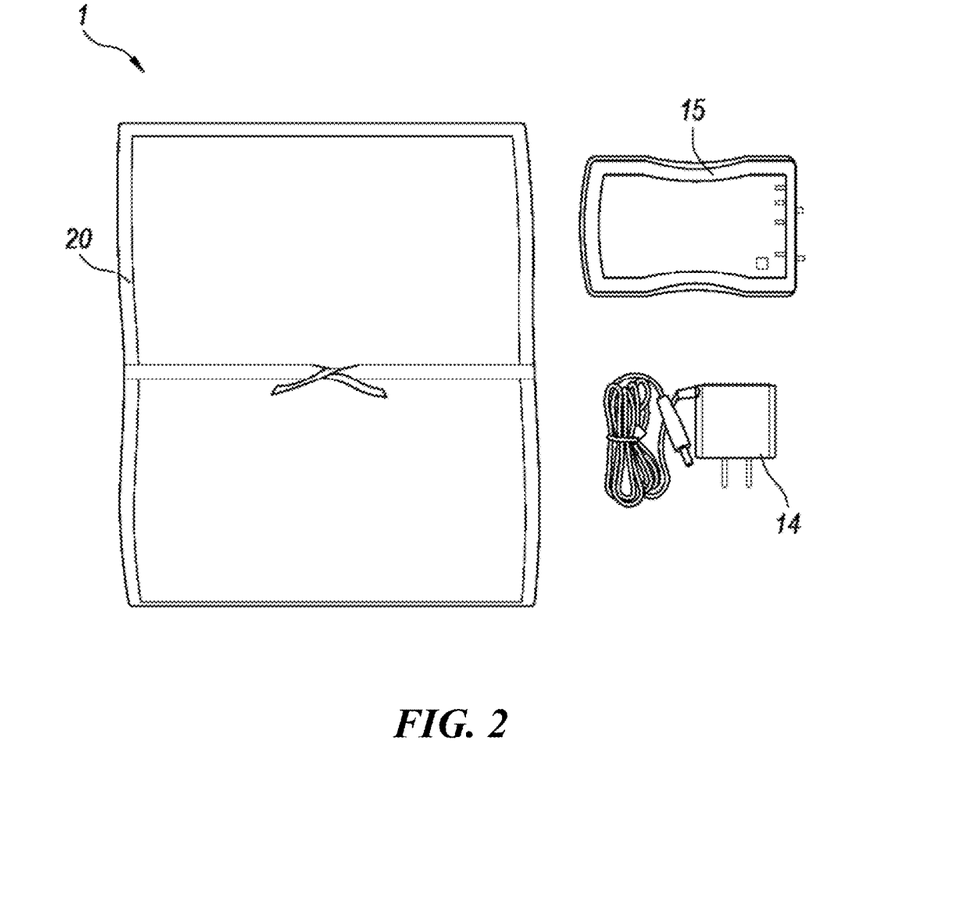
FIG. 2 illustrates an example of the ALFS system.

We have demonstrated, by using a biofield measurement instrument, that applying attenuated low-frequency stimulation (ALFS) of chakra-stimulating frequencies, herein called "relaxique frequencies," to a living body can also promote biophoton coherence. Accordingly, referring now to FIGS. 2A, 2B and 2C, the technology introduced here relates to an AFLS system and technique for elevating, tuning and/or stabilizing a living body's biofield by transmitting electrical signals at relaxique frequencies into an insulated wire antenna 39 embedded within a soft pad 20 that the subject (person or animal) lies upon during operation of the system. Hence, the system is completely non-invasive and non-touching to the user. The antenna 39 can made of a length of 24 AWG wire, for example, or other construction, and embedded into cloth designs. The pad 20 with embedded antenna 39 are arranged so that the antenna 39 is spatially aligned to specific chakras.

The ALFS system 1 introduced here, according to at least one embodiment, includes three major components, as shown in FIG. 2: an AC-to-DC power adapter 14, a roughly palm-sized transmitter electronics unit 15, and a flexible pad 20. The pad 20 contains the insulated antenna 39 (not shown in FIG. 1), which can be removably connected to the antenna output of the transmitter electronics unit 15.

The pad 20 can be placed upon a mattress with a sheet or mattress topper securing the pad 20 position. The pad 20 can also be placed on a physician's examination table or other table type with a sheet or covering securing the pad 20 position. Additionally, the ALFS system pad 20 can be positioned under a veterinary mat for animal use, or under a pet bed such as a dog bed or kennel.

Figure 3A:
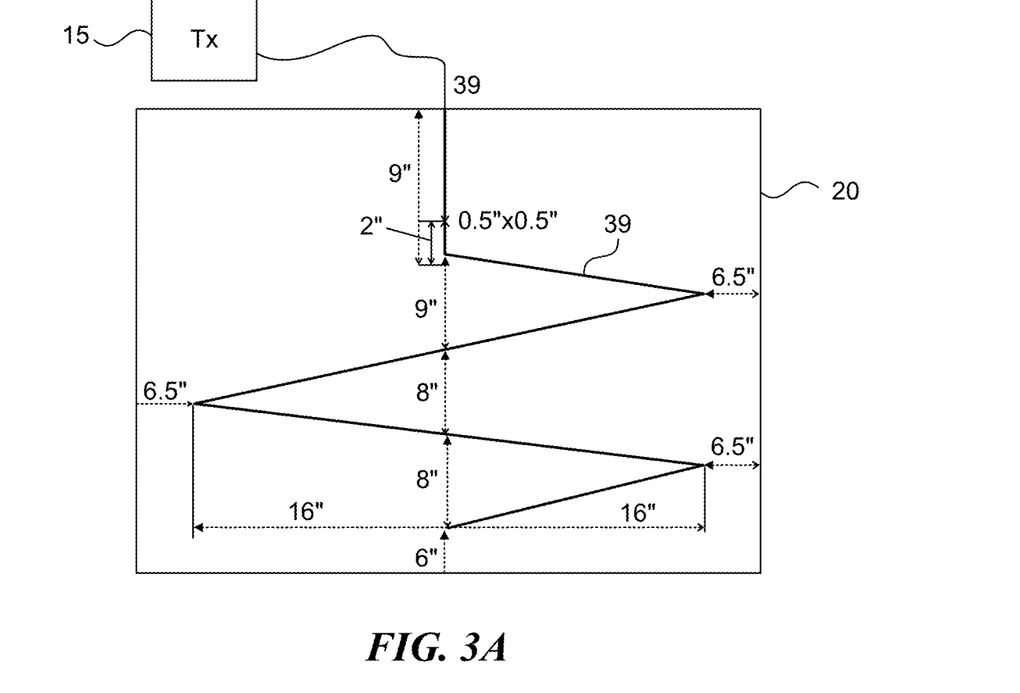
FIG. 3A schematically shows an example of a pad with embedded antenna wire in an embodiment designed for sleep use.
Figure 3B:
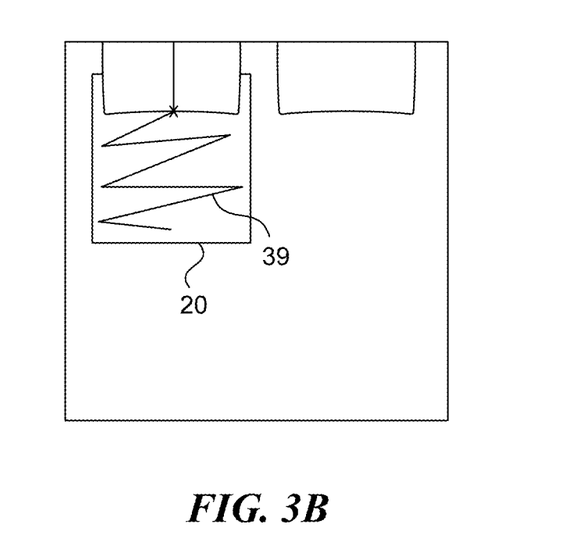
FIG. 3B shows an example of the pad of FIG. 3A deployed on a bed.
Figure 3C:
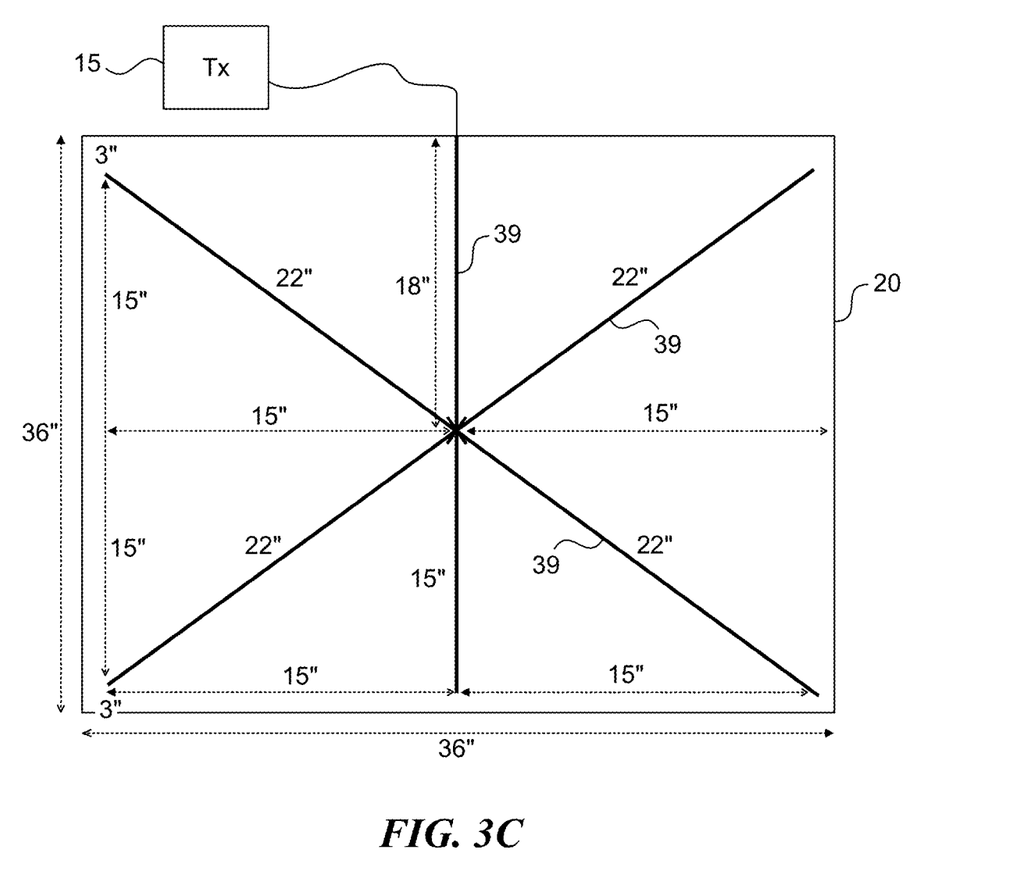
FIG. 3C schematically shows an example of a pad with embedded antenna wire in an embodiment designed for clinical use.

The insulated antenna 39 covers an area corresponding to the chakra locations indicated in FIG. 1, as illustrated in FIGS. 3A, 3B and 3C. FIGS. 3A and 3B show an embodiment of pad 20 designed for sleep use. The design for sleep use is intended predominantly to stimulate the higher chakras. The pad 20 can be, for example, muslin organic cloth 45 in.×40 in. The illustrated pattern is an example of the placement of the antenna 39. The wire can be cut to 180 in. in length, for example, and positioned under a bias tape that is sewn into the pad 20. This length of 180 in. is the wavelength corresponding to 65.5 MHz, however, any wire cut length that sets wavelengths corresponding to the 62 MHz to 78 MHz range would also work. The pad 20 can be positioned directly on a mattress, where position "X" in FIGS. 3A and 3B corresponds to the center of the pillow seam 2B—this point aligns to the throat chakra (FIG. 1).

FIG. 3C shows an embodiment of pad 20 designed for clinical use, which is predominantly targeted to the lower chakras. The pad 20 can be, for example, muslin organic cloth 36 in.×36 in. The pattern marks an example of the placement of the antenna 39 of length 180 in., for example. The wire can be positioned under a bias tape that is sewn into the cloth. The pad 20 can be positioned directly on a physician's table or other table, where the "X" formed by the antenna 39 aligns to the root chakra location (FIG. 1).

The electronics unit 15 modulates relaxique frequencies onto a low power RF carrier signal that is transmitted onto the antenna 39 at very low power levels, for example, a 200 mV signal full gain on a 9V peak-to-peak 28 KHz carrier for sleep-related uses, or a 400 mV signal full gain on a 9V peak-to-peak 28 KHz carrier for clinical uses. It is believed that a carrier signal with a frequency anywhere within the range of 13 KHz to 30 KHz is acceptable for this purpose. The modulated relaxique frequencies output signals, as purely electromagnetic signals, are not audible to the subject.

Figure 4:
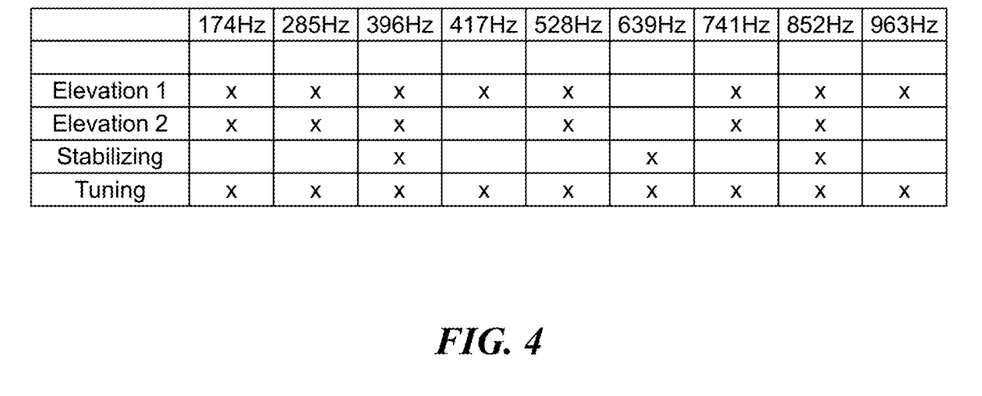
FIG. 4 shows an example of four playlists of relaxique frequencies.

The ALFS system 1 can generate relaxique (modulation) frequencies comprising nine solfeggio tones at, for example, 174 Hz, 285 Hz, 396 Hz, 417 Hz, 528 Hz, 639 Hz, 741 Hz, 852 Hz, 963 Hz, and harmonics of each of these. These tones can be partitioned into a programmable playlist for use in biofield elevation, tuning and/or stabilization, as shown in the example of FIG. 4. Combinations of one or more of these playlists can be used for different purposes, such as sleep management, relaxation, anxiety relief or clinical treatment for conditions such as pain management, depression and autoimmune issues.

FIG. 4 shows an example of four different playlists of relaxique frequencies thought to be beneficial for promoting biofield coherence. The playlists are designated Elevation 1, Elevation 2, Stabilizing and Tuning. Each playlist is characterized by the transmission (sequentially and/or concurrently) of one or more specific relaxique frequencies onto the antenna 39 by the transmitter electronics unit 15, as shown. The tones in each playlist may be played (generated and transmitted) sequentially left to right, and the playlists may be played sequentially top to bottom, for example. The Elevation 1 and Elevation 2 playlists are both designed to elevate biofield energies. The Elevation 1 is designed for sleep use, whereas the Elevation 2 playlist is designed for clinical use. The Stabilization playlist is designed to stabilize the biofield. This can be played after Elevation 2 in clinical protocol or after Tuning in sleep protocol. The Tuning playlist is, in at least one embodiment, a 63-minute playlist that plays each relaxique frequency in turn for a 7-minute duration. Tuning may follow the Elevation 1 playlist in the sleep protocol. In various embodiments, each solfeggio tone is played individually such as in the Tuning playlist, or as multiple sequencing tones such as triplets and other multiple tones as in the Elevation 1, Elevation 2 and Stabilizing playlists. The duration of each tone in each playlist can be configured as desired by the user or manufacturer of the system. In at least some embodiments, the configured and/or recommended durations are as follows: For sleep use the use period can be 195 minutes in length, which gets repeated until the electronics unit 15 is switched off. More specifically, the use period can include Elevation 1 for 120 minutes, followed by Stabilization for 50 minutes and then Tuning for 63 minutes. For clinical use, the use period can be much shorter, e.g., 45 minutes in length, which includes Elevation 2 for 35 minutes and Stabilization for 10 minutes. Other combinations of playlists and durations are also possible.

Figure 5:
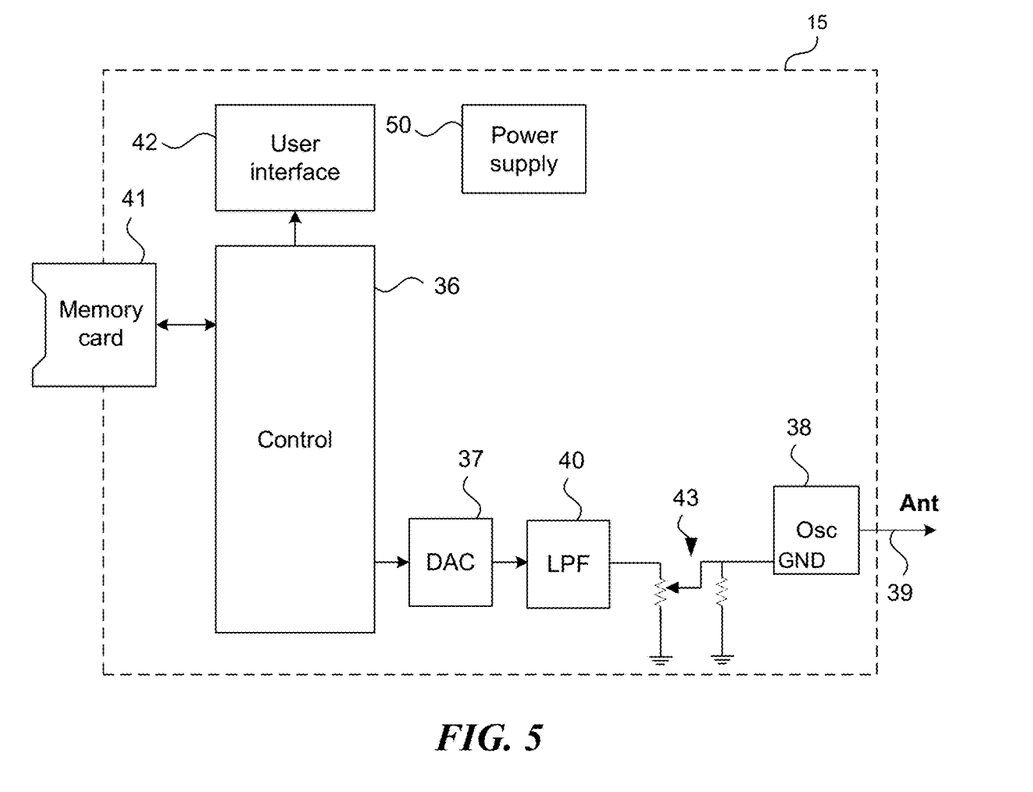
FIG. 5 is a block diagram showing internal components of the electronics unit of the system.

FIG. 5 is a block diagram of the internal components of the electronics unit 15, according to at least one embodiment. The electronics unit 15 shown in FIG. 2 comprises one or more power supplies 50, control circuitry 36, a digital-to-analog converter (DAC) with included audio decoder 37, oscillator circuitry 38, and a user interface 42. Each power supply 50 is designed for low electromagnetic interference (EMI). The control circuitry 36 is programmed to read from a playlist of relaxique frequency tones 35 that, in at least one embodiment, are programmed into an insertable secure digital memory card 41 (e.g., an SD card) in a digital audio format, such as MP3 or WAVE, and decoded into serial analog audio data 46 such as I2S. In other embodiments, the electronic unit 15 may contain its own non-volatile storage such as an internal hard drive to store the playlists. The control circuitry 36 generates the relaxique frequency tones according to the playlist as digital signals, which are provided to the DAC 37, where volume control can be implemented for relaxique frequency amplitude adjustment (e.g., by adjustment of a gain control on the user interface 42). In various embodiments, the control circuitry 36 may be or include a Digital Signal Processor (DSP), programmable microcontroller, Application Specific Integrated Circuit (ASIC), Programmable Logic Device (PLD), Field Programmable Gate Array (FPGA), or other known or convenient type of device, or a combination of such devices.

The audio data output by the control circuitry 36 is converted to analog form by the DAC 37 and then passed to a low-pass filter 40, which filters out distortion. The output of the low-pass filter 40 is connected to a resistor splitter network 43, one end of which is coupled directly to the Vss pin of the oscillator (which would be connected to ground in most current-controlled oscillator designs) and the other end of which is connected to ground. The oscillator generates a 28 KHz carrier signal. This connection configuration injects the analog audio as a mono audio channel into the ground currents as a way of amplitude modulation of the 28 KHz carrier signal. The output of the oscillator 38 is passed to the antenna 39. This connection configuration creates a very low-power RF signal comprising an amplitude modulated (AM) signal (e.g., 200 mV peak-to-peak at full gain) modulated onto a carrier (9 V peak-to-peak) that presents the relaxique tones to the subject at a power level comparable to the energy levels of the subject's biofield.

In other embodiments, other carrier frequencies that extend beyond the highest relaxique frequency 35 can be used. Further, in other embodiments, stereo channels or other multi-channel audio can be used.

The oscillator 38 can comprise, for example, logic gates configured as a current-controlled oscillator to generate a 28 KHz square wave signal or other frequency. In other embodiments, a Schmitt trigger or ring oscillator can be used to generate the carrier frequency. In further embodiments, a central processing unit (CPU) and digital audio decoding circuitry such as an MP3 or WAVE decoder can be implemented. Though shown separately in FIG. 5, in some embodiments the DAC 37 may be integrated with the control circuitry 36. Further, it is possible to combine additional components of the transmitter electronics unit 15. The storage device 41 can be or include, for example, an SD card, but can alternatively or additionally can be or include any of various forms of storage, including random access memory (RAM), read-only memory (ROM), flash memory, hard disk drive, digital versatile disk (DVD) drive, removable storage such as one or more USB drives, or the like, or combination thereof.

The user interface 42 can be very simple, such as a set of labeled mechanical buttons, switches and light-emitting diodes (LEDs). Alternatively, the user interface can be more sophisticated; for example, it may include a more detailed display, which can be a full color touch-screen display. Alternatively, or additionally, the electronics unit 15 may be capable of being connected (via cabling or wirelessly) to a separate display device and/or input devices, or to an external computer that has a display device and input devices, which can be used to implement the user interface 42.

The ALFS system 1 comprises a gain control located on the user interface 42 to adjust the amplitude of the relaxique frequencies that are transmitted onto the carrier signal. Transmission can be initiated by a switch or other suitable control located on the user interface 42, for example, and can be configured by a user to continuously cycle through some or all of the playlists until switched off, or until a user-programmable timer expires.

Figure 6:
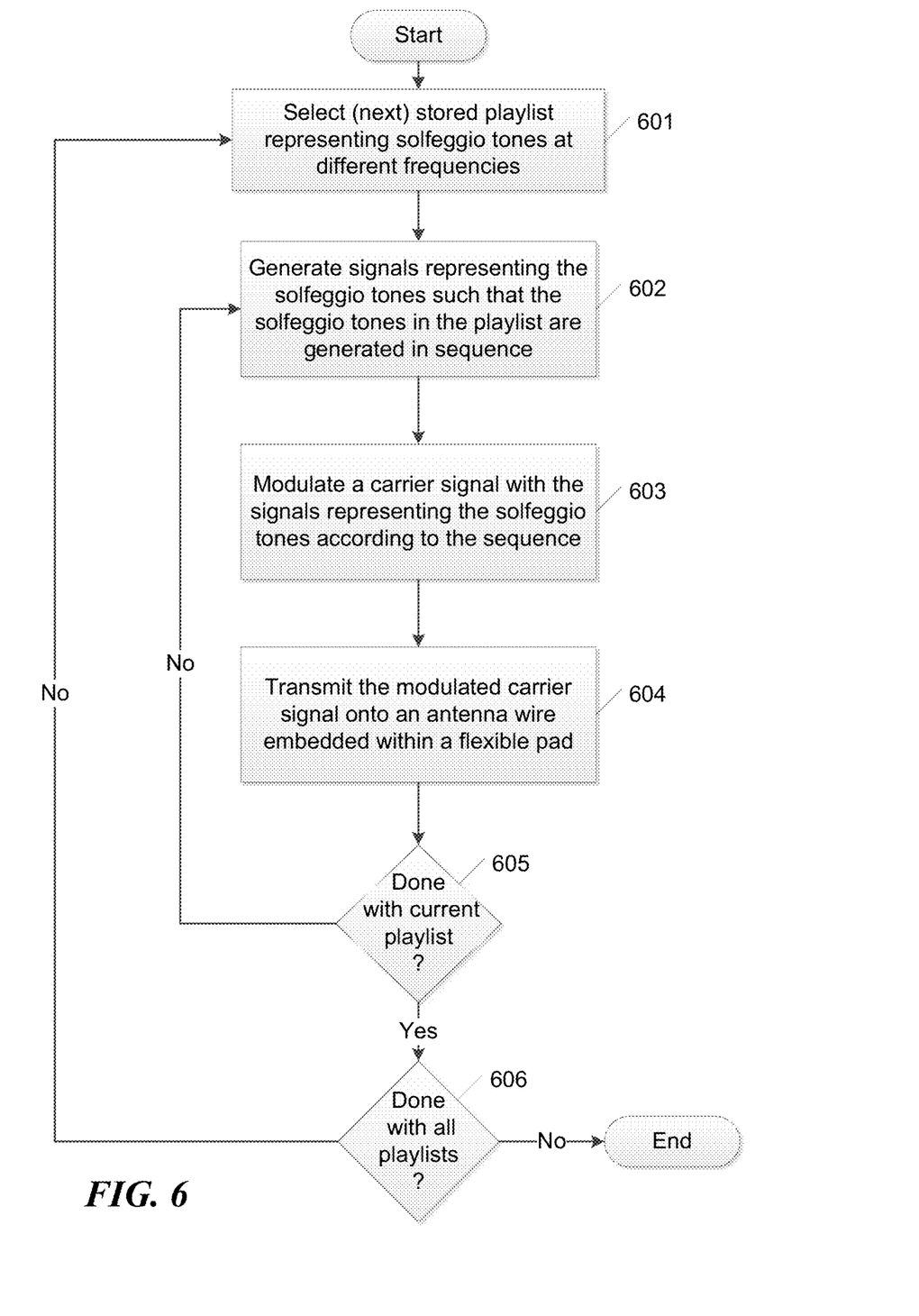
FIG. 6 is a flowchart showing an example of an overall process that may be performed by the electronics unit.

FIG. 6 is a flowchart showing an example of an overall process that may be performed by the electronics unit 15 of the ALFS system 1. Initially, at step 601 the electronics unit 15 selects a stored playlist that specifies a sequence of solfeggio tones at different frequencies. During the first iteration of this step, the selected playlist may be the first playlist in a specified sequence of playlists, such as shown in FIG. 4. At step 602, the electronics unit 15 generates signals representing the solfeggio tones such that the tones in the playlists are generated in sequence. Note, however, that some tones in the sequence may also be played concurrently, and harmonics of various tones may be played concurrently with certain tones. At step 603, the electronics unit 15 modulates the carrier signal with the generated signals representing the solfeggio tones, according to the sequence. At step 604 the electronics unit 15 transmits the modulated carrier signal onto the antenna wire 39 embedded within the flexible pad 20. Note that as the system continues to operate, execution of steps 602, 603 and 604 can occur concurrently. After a specified time interval, or from time to time, the electronics unit 15 checks at step 605 whether the current playlist is complete. If the playlist is not complete, the process loops back to step 602. If the playlist is complete, then the process proceeds to step 606, in which the electronics unit 15 checks whether all of the stored playlists have been completed. If all of the playlists have not been completed, the process loops back to step 601 to select and play the next playlist. Otherwise, the process ends. Note that in some embodiments, however, the electronics unit 15 may be configured to play only a specified subset of the available playlists, rather than all of them.

Figure 7A:
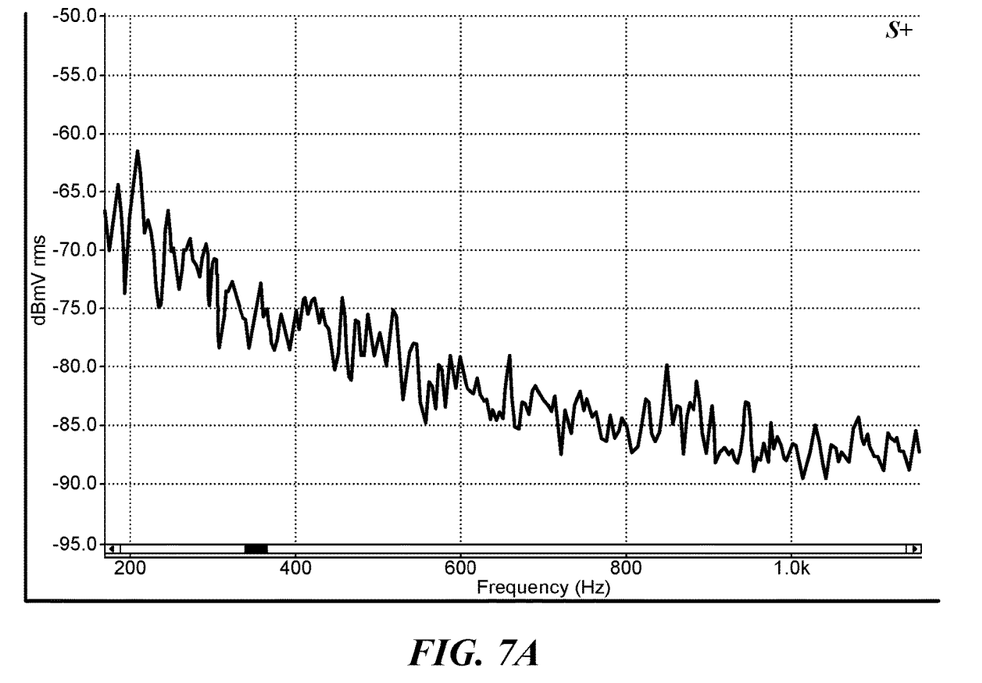
FIG. 7A shows a spectral plot of a subject measured by the biofield measurement instrument immediately before using the ALFS system.
Figure 7B:
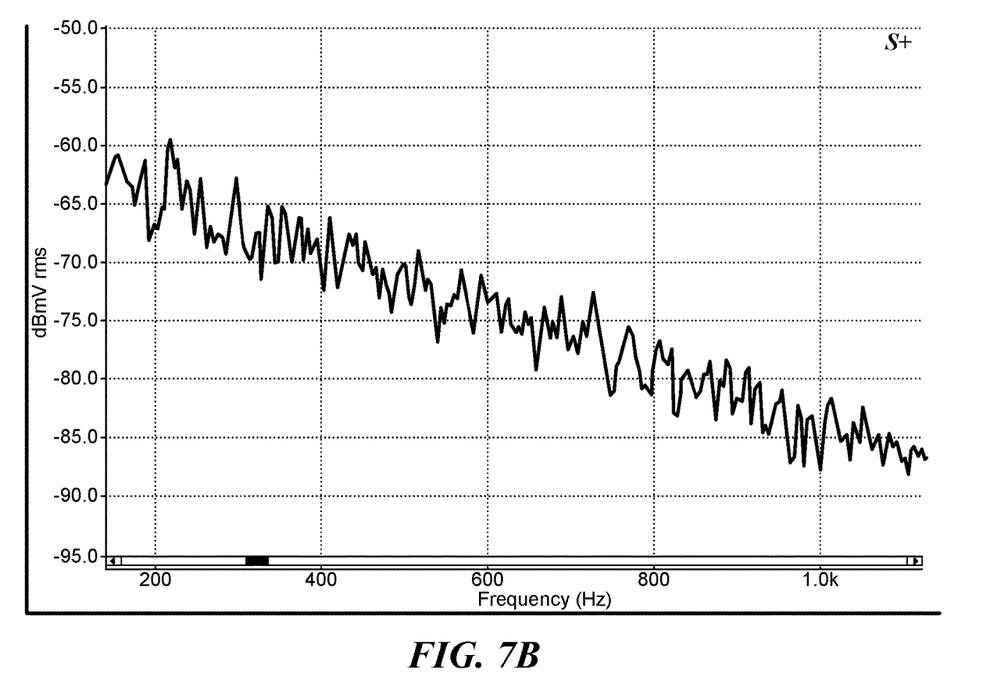
FIG. 7B shows a spectral plot of the same subject as in FIG. 7A, as measured by the biofield measurement instrument immediately after the Elevation 1 playlist has been applied to the subject.

FIGS. 7A and 7B show an example of a spectral response as can be measured by a biofield measurement instrument before and after, respectively, using a ALFS system and technique such as disclosed herein. Specifically, FIG. 7A shows the spectral plot of a subject measured by the biofield measurement instrument immediately before using the ALFS system 1 and technique on the subject, with gain set to 200 mV and the Elevation 1 frequencies playlist (FIG. 4) selected. FIG. 7B shows the spectral plot of the same subject measured by the biofield measurement instrument with the same gain setting immediately after the Elevation 1 playlist has been applied to the subject by the disclosed ALFS system 1 and technique for 20 minutes, using pad design and placement as shown in FIGS. 3A and 3B. The plot shows an increase in energies of approximately 5 dBm $V_{RMS}$ across 200 to 800 Hz bandwidth.

The machine-implemented operations described above can be implemented, at least in part, by programmable circuitry programmed/configured by software and/or firmware, or entirely by special-purpose circuitry, or by a combination of such forms. Such special-purpose circuitry (if any) can be in the form of, for example, one or more application-specific integrated circuits (ASICs), programmable logic devices (PLDs), field-programmable gate arrays (FPGAs), system-on-a-chip systems (SOCs), etc.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and that (ii) the components of respective embodiments may be combined in any manner.

EXAMPLES

The following examples of the technology disclosed herein are contemplated:

1. A system comprising: a flexible pad; an antenna wire disposed within the flexible pad; and an electronics unit connected to or capable of being connected to the antenna wire, the electronics unit including control circuitry configured to access a stored playlist representing a sequence of tones at different frequencies, and generate digital signals representing the tones such that two or more of the tones are generated in the sequence according to the stored playlist; a digital-to-analog converter to convert the digital signals representing the tones to analog signals representing the tones; and an oscillator to generate a carrier signal and coupled so that the analog signals representing the tones modulate the carrier signal according to the sequence when the analog signals representing the tones are applied to an input of the oscillator, the oscillator having an output connected to transmit the modulated carrier signal onto the antenna wire.

2. A system as recited in example 1, wherein the antenna is disposed within the pad so as to align spatially with a chakra point of a subject when the subject lies upon the pad.

3. A system as recited in example 1 or example 2, wherein the antenna is disposed within the pad so as to align spatially with a plurality of chakra points of a subject when the subject lies upon the pad.

4. A system as recited in any of examples 1 through 3, further comprising a low-pass filter coupled between an output of the digital-to-analog converter and the input of the oscillator.

5. A system as recited in any of examples 1 through 4, further comprising a resistor splitter network coupled to an output of the low-pass filter and to the input of the oscillator, wherein the input of the oscillator is a power supply pin of the oscillator.

6. A system as recited in any of examples 1 through 5, wherein the oscillator is coupled so that the analog signals representing the tones are injected into a ground current of the oscillator.

7. A system as recited in any of examples 1 through 6, wherein the carrier signal is in the range of 13 KHz to 30 KHz and is less than 10 V peak-to-peak, and the oscillator outputs onto the antenna a signal of less than 500 mV full gain on the carrier signal.

8. A system as recited in any of examples 1 through 7, wherein the carrier signal is 28 KHz and is 9 V peak-to-peak, and the oscillator outputs onto the antenna a signal of no more than 400 mV full gain on the carrier signal.

9. A system as recited in any of examples 1 through 8, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

10. A system as recited in any of examples 1 through 9, wherein the control circuitry is configured to select a playlist from amongst a plurality of stored playlists, wherein each of the plurality of stored playlists represents a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz.

11. An electronics unit comprising: circuitry configured to access a stored playlist representing a sequence of tones at different frequencies, and to generate signals representing the tones such that two or more of the tones are generated in the sequence according to the stored playlist; and an oscillator to generate a carrier signal and coupled so that the signals representing the tones modulate the carrier signal according to the sequence when applied to an input of the oscillator, the oscillator having an output connected to transmit the modulated carrier signal onto an antenna when the electronics unit is in operation.

12. An electronics unit as recited in example 11, wherein the oscillator is coupled so that the signals representing the tones are injected into a ground current of the oscillator.

13. An electronics unit as recited in example 11 or example 12, wherein the carrier signal is in the range of 13 KHz to 30 KHz and is less than 10 V peak-to-peak, and the oscillator outputs onto the antenna a signal of less than 500 mV full gain on the carrier signal.

14. An electronics unit as recited in any of examples 11 through 13, wherein the control circuitry is configured to select a playlist from amongst a plurality of stored playlists, wherein each said playlist represents a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz.

15. An electronics unit as recited in any of examples 11 through 14, wherein the carrier signal is 28 KHz and is 9 V peak-to-peak, and the oscillator outputs onto the antenna a signal of no more than 400 mV full gain on the carrier signal.

16. An electronics unit as recited in any of examples 11 through 15, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

17. An electronics unit as recited in any of examples 11 through 16, wherein the control circuitry is configured to select a playlist from amongst a plurality of stored playlists, wherein each said playlist represents a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz.

18. A method comprising: accessing a stored playlist representing a sequence of solfeggio tones at different frequencies; generating signals representing the solfeggio tones such that two or more of the solfeggio tones are generated in the sequence according to the stored playlist; modulating a carrier signal with the signals representing the solfeggio tones according to the sequence; and transmitting the modulated carrier signal onto an antenna wire embedded within a flexible pad.

19. A method as recited in example 18, wherein the antenna is disposed within the pad so as to align spatially with a chakra point of a subject when the subject lies upon the pad.

20. A method as recited in example 18 or example 19, further comprising: causing a subject to be disposed on the flexible pad so that the antenna wire spatially aligns with a plurality of chakra points of the subject.

21. A method as recited in any of examples 18 through 20, wherein said modulating comprises injecting the signals representing the solfeggio tones into a ground current of an oscillator that generates the carrier signal.

22. A method as recited in any of examples 18 through 21, wherein the carrier signal is in the range of 13 KHz to 30 KHz and is less than 10 V peak-to-peak, and the signals representing the solfeggio tones are modulated at less than 500 mV full gain onto the carrier signal.

23. A method as recited in any of examples 18 through 22, wherein the carrier signal is 28 KHz and is 9 V peak-to-peak, and the signals representing the solfeggio tones are modulated at no more than 400 mV full gain onto the carrier signal.

24. A method as recited in any of examples 18 through 23, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

25. A method as recited in any of examples 18 through 24, wherein the storage facility comprises a plurality of stored playlists, each representing a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz; the method further comprising accessing the plurality of playlists and playing the plurality playlists in a specified sequence.

Unless contrary to physical possibility, it is envisioned that (i) the methods/steps described herein may be performed in any sequence and/or in any combination, and that (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A system for attenuated low-frequency stimulation (ALFS) of a body's chakra points, the system comprising:
   a flexible pad;
   an antenna wire disposed within the flexible pad; and
   an electronics unit connected to or capable of being connected to the antenna wire, the electronics unit including
      control circuitry configured to
         access a stored playlist representing a sequence of tones at different frequencies, and
         generate digital signals representing the tones such that two or more of the tones are generated in the sequence according to the stored playlist;
      a digital-to-analog converter to convert the digital signals representing the tones to analog signals representing the tones; and
      an oscillator to generate a carrier signal and coupled so that the analog signals representing the tones modulate the carrier signal according to the sequence when the analog signals representing the tones are applied to an input of the oscillator, the oscillator having an output connected to transmit the modulated carrier signal onto the antenna wire;
      wherein the carrier signal is in the range of 13 KHz to 30 KHz and is less than 10 V peak-to-peak, and the oscillator outputs onto the antenna a signal of less than 500 mV full gain on the carrier signal.

2. The system as recited in claim 1, wherein the input of the oscillator is a ground terminal of the oscillator.

3. The system as recited in claim 1, wherein the antenna is disposed within the pad such that the antenna is configured to be spatially aligned with a plurality of chakra points of a subject when the subject lies upon the pad.

4. The system as recited in claim 1, further comprising a low-pass filter coupled between an output of the digital-to-analog converter and the input of the oscillator.

5. The system as recited in claim 4, further comprising a resistor splitter network coupled to an output of the low-pass filter and to the input of the oscillator, wherein the input of the oscillator is a power supply pin of the oscillator.

6. A system as recited in claim 1, wherein the analog signals representing the tones are injected into a ground current of the oscillator.

7. The system as recited in claim 1, wherein the carrier signal is 28 KHz and is 9 V peak-to-peak, and the oscillator outputs onto the antenna a signal of no more than 400 mV full gain on the carrier signal.

8. The system as recited in claim 1, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

9. The system as recited in claim 1, wherein the control circuitry is configured to select a playlist from amongst a plurality of stored playlists, wherein each of the plurality of stored playlists represents a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz.

10. A method for attenuated low-frequency stimulation (ALFS) of a body's chakra points, the method comprising:
    accessing a stored playlist representing a sequence of solfeggio tones at different frequencies;
    generating signals representing the solfeggio tones such that two or more of the solfeggio tones are generated in the sequence according to the stored playlist;
    modulating a carrier signal with the signals representing the solfeggio tones according to the sequence; and
    transmitting the modulated carrier signal onto an antenna wire embedded within a flexible pad;
    wherein the carrier signal is in the range of 13 KHz to 30 KHz and is less than 10 V peak-to-peak, and the signals representing the solfeggio tones are modulated at less than 500 mV full gain onto the carrier signal.

11. The method as recited in claim 10, further comprising applying the signals representing the solfeggio tones to a ground terminal of an oscillator that performs said modulating.

12. The method as recited in claim 10, further comprising:
    causing a subject to be disposed on the flexible pad so that the antenna wire spatially aligns with a plurality of chakra points of the subject.

13. The method as recited in claim 10, wherein said modulating comprises injecting the signals representing the solfeggio tones into a ground current of an oscillator that generates the carrier signal.

14. The method as recited in claim 10, wherein the carrier signal is 28 KHz and is 9 V peak-to-peak, and the signals representing the solfeggio tones are modulated at no more than 400 mV full gain onto the carrier signal.

15. The method as recited in claim 10, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

16. The method as recited in claim 10, wherein the storage facility comprises a plurality of stored playlists, each representing a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz;
    the method further comprising accessing the plurality of playlists and playing the plurality playlists in a specified sequence.

17. A system for attenuated low-frequency stimulation (ALFS) of a body's chakra points, the system comprising:
    a flexible pad;
    an antenna wire disposed within the flexible pad; and
    an electronics unit connected to or capable of being connected to the antenna wire, the electronics unit including
       control circuitry configured to access a stored playlist representing a sequence of tones at different frequencies, and generate digital signals representing the tones such that two or more of the tones are generated in the sequence according to the stored playlist;

a digital-to-analog converter to convert the digital signals representing the tones to analog signals representing the tones;

an oscillator to generate a carrier signal and coupled so that the analog signals representing the tones modulate the carrier signal according to the sequence when the analog signals representing the tones are applied to an input of the oscillator, the oscillator having an output connected to transmit the modulated carrier signal onto the antenna wire;

a low-pass filter coupled between an output of the digital-to-analog converter and the input of the oscillator; and a resistor splitter network coupled to an output of the low-pass filter and to the input of the oscillator, wherein the input of the oscillator is a power supply pin of the oscillator.

18. The system as recited in claim 17, wherein the input of the oscillator is a ground terminal of the oscillator.

19. The system as recited in claim 17, wherein the analog signals representing the tones are injected into a ground current of the oscillator.

20. The system as recited in claim 17, wherein the carrier signal is in the range of 13 KHz to 30 KHz and is less than 10 V peak-to-peak, and the oscillator outputs onto the antenna a signal of less than 500 mV full gain on the carrier signal.

21. The system as recited in claim 17, wherein the carrier signal is 28 KHz and is 9 V peak-to-peak, and the oscillator outputs onto the antenna a signal of no more than 400 mV full gain on the carrier signal.

22. The system as recited in claim 17, wherein the playlist represents a sequence of tones having at least three of the following frequencies: 174 Hz, 285 Hz, 396 Hz, 417 Hz, 528 Hz, 639 Hz, 741 Hz, 852 Hz, 963 Hz.

23. The system as recited in claim 17, wherein the control circuitry is configured to select a playlist from amongst a plurality of stored playlists, wherein each of the plurality of stored playlists represents a different sequence of tones, each sequence having tones of at least three of the following frequencies: 174 Hz, 285 Hz, 396 Hz, 417 Hz, 528 Hz, 639 Hz, 741 Hz, 852 Hz, 963 Hz.

* * * * *